(12) United States Patent
Wang

(10) Patent No.: US 7,796,870 B2
(45) Date of Patent: Sep. 14, 2010

(54) LIGHTING CONTROL FOR IN VIVO CAPSULE CAMERA

(75) Inventor: Kang-Huai Wang, Saratoga, CA (US)

(73) Assignee: Capso Vision, Inc., Saratoga, CA (US)

( * ) Notice: Subject to any disclaimer, the term of this patent is extended or adjusted under 35 U.S.C. 154(b) by 506 days.

(21) Appl. No.: 11/623,601

(22) Filed: Jan. 16, 2007

(65) Prior Publication Data

US 2008/0170846 A1 Jul. 17, 2008

(51) Int. Cl.
*G03B 29/00* (2006.01)
*A61B 1/04* (2006.01)

(52) U.S. Cl. .......................... 396/14; 396/17; 396/182; 600/109

(58) Field of Classification Search ................... 396/17, 396/182, 14; 348/65, 76, 222.1, 68, 77; 600/109, 600/118
See application file for complete search history.

(56) References Cited

U.S. PATENT DOCUMENTS

| 7,116,352 | B2 | 10/2006 | Yaron |
| 7,144,366 | B2 | 12/2006 | Takizawa et al. |
| 2003/0117491 | A1* | 6/2003 | Avni et al. ................... 348/77 |
| 2004/0190154 | A1 | 9/2004 | Wakai et al. |
| 2005/0043586 | A1* | 2/2005 | Suzushima ................. 600/160 |
| 2005/0270381 | A1* | 12/2005 | Owens et al. ............. 348/222.1 |
| 2006/0195014 | A1 | 8/2006 | Seibel et al. |

FOREIGN PATENT DOCUMENTS

JP 2005000552 A * 1/2005

* cited by examiner

*Primary Examiner*—Christopher E Mahoney
*Assistant Examiner*—Autumn Parker
(74) *Attorney, Agent, or Firm*—Haynes and Boone, LLP

(57) ABSTRACT

A method for controlling a lighting source in a capsule camera improves image quality by avoiding over-exposure or under-exposure in all regions of an image, while concurrently reducing significantly power dissipation in the capsule camera. A capsule camera using the method includes: (1) one or more sensor arrays each having one or more pixels in one or more designated regions in the field of view of the capsule camera; (2) lighting elements each providing illumination to one or more of the designated regions; and (3) a control unit that (a) extracts a parameter value from the pixels of each region; (b) evaluates the parameter value at each region; and (c) adjusts the lighting elements providing illumination to each region according to the evaluation. The parameter value may be an average value of the pixels. The purpose of the adjustment is to bring the parameter value for the region to within a predetermined range. In one embodiment, the control unit adjusts an amount of light provided by each lighting element, which may be given by integrating a light intensity of the lighting element over time. In one implementation, the light intensity in each lighting element is substantially constant and the control unit adjusts an exposure time for each lighting element. The lighting element may be, for example, a light emitting diode.

54 Claims, 11 Drawing Sheets

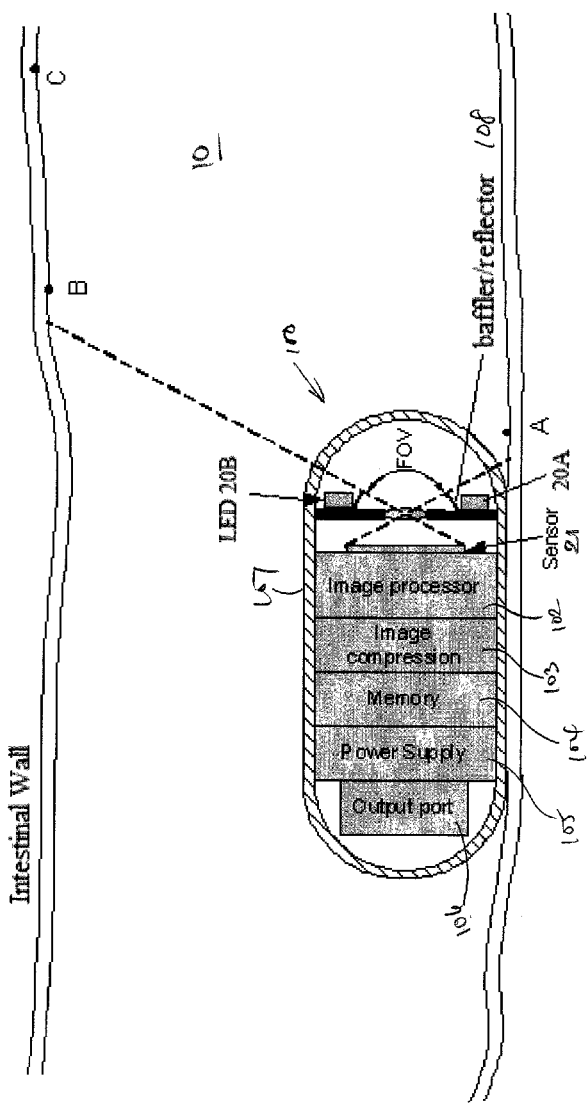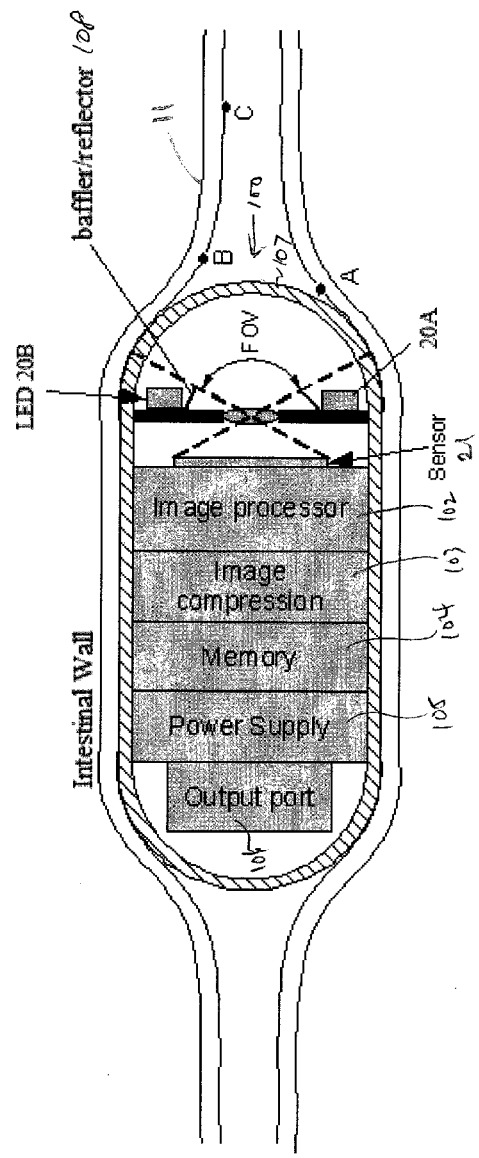
FIGURE 1A
FIGURE 1B

LIGHTING CONTROL FOR IN VIVO CAPSULE CAMERA

BACKGROUND OF THE INVENTION

1. Field of the Invention

The present invention relates to swallowable capsule cameras for imaging of the gastro-intestinal (GI) tract. In particular, the present invention relates to the control of the light sources in the camera.

2. Discussion of the Related Art

Devices for imaging body cavities or passages in vivo are known in the art and include endoscopes and autonomous encapsulated cameras. Endoscopes are flexible or rigid tubes that are passed into the body through an orifice or surgical opening, typically into the esophagus via the mouth or into the colon via the rectum. An image is taken at the distal end using a lens and transmitted optically to the proximal end located outside the body, either by a lens-relay system or by a coherent fiber-optic bundle. Alternatively, an instrument may record an image electronically at the distal end (e.g., using a CCD or CMOS array) and transfers the image data electrically to the proximal end through a cable. Endoscopes allow a physician control over the field of view and are well-accepted diagnostic tools. However, they have a number of limitations, present risks to the patient, and are invasive and uncomfortable for the patient. The cost of these procedures restricts their application as routine health-screening tools.

Because of the difficulty traversing a convoluted passage, endoscopes cannot reach the majority of the small intestine and special techniques and precautions—that increase cost—are required to reach the entirety of the colon. Endoscopic risks include the possible perforation of the bodily organs traversed and complications arising from anesthesia. Moreover, a trade-off must be made between patient pain during the procedure and the health risks and post-procedural downtime associated with anesthesia. Therefore, endoscopy is necessarily an in-patient service that involves a significant amount of time from clinicians and thus is a costly procedure.

An alternative in vivo image sensing technique is capsule endoscopy. In capsule endoscopy, a camera is housed in a swallowable capsule, along with a radio transmitter for transmitting data (which consists primarily of images recorded by the camera) to a base-station receiver or transceiver in a data recorder located outside the body. The capsule may also include a radio receiver for receiving instructions or other data from a base-station transmitter. Instead transmitting in a radio frequency, lower frequency electromagnetic signals may be used. Power may be supplied inductively from an external inductor to an internal inductor within the capsule or from a battery within the capsule.

An early example of a camera in a swallowable capsule is described in the U.S. Pat. No. 5,604,531, issued to the Ministry of Defense, State of Israel. A number of patents assigned to Given Imaging describe more details of such a system, using a transmitter to send the camera images to an external receiver. Examples are disclosed in U.S. Pat. Nos. 6,709,387 and 6,428,469. There are also a number of patents to the Olympus Corporation describing a similar technology. For example, U.S. Pat. No. 4,278,077 shows a capsule with a camera for the stomach, which includes film in the camera. U.S. Pat. No. 6,800,060 shows a capsule which stores image data in an atomic resolution storage (ARS) device.

An advantage of an autonomous encapsulated camera with an internal battery is that the measurements may be made with the patient ambulatory, out of the hospital, and with only moderate restrictions of activity. The base station includes an antenna array surrounding the bodily region of interest and this array can be temporarily affixed to the skin or incorporated into a wearable vest. A data recorder is attached to a belt and includes a battery power supply and a data storage medium for saving recorded images and other data for subsequent uploading onto a diagnostic computer system.

A typical procedure consists of an in-patient visit in the morning during which clinicians attach the base station apparatus to the patient and the patient swallows the capsule. The system records images beginning just prior to swallowing and records images of the GI tract until its battery completely discharges. Peristalsis propels the capsule through the GI tract. The rate of passage depends on the degree of motility. Usually, the small intestine is traversed in 4 to 8 hours. After a prescribed period, the patient returns the data recorder to the clinician who then uploads the data onto a computer for subsequent viewing and analysis. The capsule is passed in time through the rectum and need not be retrieved.

The capsule camera allows the GI tract from the esophagus down to the end of the small intestine to be imaged in its entirety, although it is not optimized to detect anomalies in the stomach. Color photographic images are captured so that anomalies need only have small visually recognizable characteristics, not topography, to be detected. The procedure is pain-free and requires no anesthesia. Risks associated with the capsule passing through the body are minimal; certainly, the risk of perforation is much reduced relative to traditional endoscopy. The cost of the procedure is less than that of traditional endoscopy because of the decreased requirements in clinician time, clinical facilities and anesthesia.

As the capsule camera becomes a viable technology for inspecting gastrointestinal tract, various methods for storing its image data have emerged. For example, U.S. Pat. No. 4,278,077 discloses a capsule camera that stores image data in chemical films. U.S. Pat. No. 5,604,531 discloses a capsule camera that transmits image data by wireless to an antenna array attached to the body or provided inside a vest worn by the patient. U.S. Pat. No. 6,800,060 discloses a capsule camera that stores image data in an expensive atomic resolution storage (ARS) device. The stored image data may then be downloaded to a workstation, which is normally a personal computer for analysis and processing. The results may then be reviewed by a physician using a friendly user interface. However, these methods all require a physical media conversion during the data transfer process. For example, image data on chemical film are required to be converted to a physical digital medium readable by the personal computer. The wireless transmission by electromagnetic signals requires extensive processing by an antenna and radio frequency electronic circuits to produce an image that can be stored on a computer. Further, both the read and write operations in an ARS device rely on charged particle beams.

A capsule camera using a semiconductor memory device, whether volatile or nonvolatile, is capable of a direct interface with a CMOS or CCD image sensor, where the image is captured, and a personal computer, where the image may be analyzed. The high density and low manufacturing cost achieved in recent years made the semiconductor memory the most promising technology for image storage in a capsule camera. According to Moore's law, which is still believed valid, the density of integrated circuits doubles every 24 months. Meanwhile, CMOS or CCD sensor resolution continues to improve, doubling every few years. Recent advancement in electronics also facilitate development in capsule camera technology. For example, (a) size and power reductions in light emitting diodes (LEDs) promotes the use of LEDs as a lighting source for a capsule camera; (b) new CMOS image sensors also reduce power and component count; (c) the continued miniaturization of integrated circuit allows integrating many functions on a single silicon substrate (i.e., system-on-a-chip or "SOC), resulting in size and power reductions.

SUMMARY

A method for controlling a lighting source in a capsule camera improves image quality by avoiding over-exposure or under-exposure in all regions of an image, while concurrently reducing significantly power dissipation in the capsule camera.

According to one embodiment of the present invention, a capsule camera having adjustable illumination control includes: (1) one or more sensor arrays each having one or more pixels in one or more designated regions in a field of view of the capsule camera; (2) lighting elements each providing illumination to one or more of the designated regions; and (3) a control unit that (a) extracts a parameter value from the pixels of each region; (b) evaluates the parameter value at each region; and (c) adjusts the lighting elements providing illumination to each region according to the evaluation. The parameter value may be an average value of the pixels. The purpose of the adjustment is to bring the parameter value for the region to within a predetermined range. In one embodiment, the control unit adjusts an amount of light provided by each lighting element, which may be given by integrating a light intensity of the lighting element over time. In one implementation, the light intensity in each lighting element is substantially constant and the control unit adjusts an "on" time for each lighting element. The lighting element may be, for example, a light emitting diode.

Each designated region may be illuminated by multiple lighting elements. In one implementation, each lighting element illuminates a designated region driven by a common current mirror circuit. The current in each lighting element may be reflected from the common current mirror circuit by a transistor of a predetermined conductivity type.

According to one embodiment of the present invention, the capsule camera includes a motion detection circuit which compares the extracted parameter values in two exposures to detect motion of the capsule camera. The exposures may be two successive exposures of the capsule camera. In this embodiment, the control unit operates in an active mode and a monitor mode. The control unit enters the monitor mode when no motion of the capsule camera is detected in successive exposures in the active mode, and enters the active mode when motion is detected in the monitor mode. Exposures in the active mode are provided within a first range of light amounts and exposures in the monitor mode are provided in a second range of light amounts, the light amounts within the first range being substantially greater than the light amounts in the second range. The first range is provided to yield images with sufficient detail for a human reviewer to perform a diagnosis.

According to one embodiment of the present invention, in the first exposure of the monitor mode, the parameter value extracted from the last exposure in the active mode is scaled based on the first and second ranges of light amounts. The scaled parameter value is then used by the motion detection circuit in the comparison. In the monitor mode, the motion detection circuit compares the extracted parameter value for each frame against the parameter value extracted from the last exposure in the active mode. The criteria for motion detection in the active mode and in the monitor mode may be different. The criterion for motion detection for successive frames with the same exposure may also be different from the criterion for motion detection for successive frames with different amounts of exposure. Upon returning to the active mode from the monitor mode, the lighting elements are returned to settings used for taking the last frame in a previous active mode operation. One or more of the lighting elements are not activated in the monitor mode to achieve power saving goals.

According to one embodiment of the present invention, the capsule camera includes component cameras each facing a different direction, so that the fields of view of the component cameras together provide a panoramic field of view (e.g., 360-degree).

The present invention is better understood upon consideration of the detailed description below in conjunction with the drawings.

BRIEF DESCRIPTION OF THE DRAWINGS

FIG. 1A shows capsule camera 100 inside a gastrointestinal tract 10 taking measurements with its light sources 20A and 20B.

FIG. 1B shows capsule camera 100 in narrow portion 11 of GI tract 10.

To facilitate cross-references, like elements in the figures are assigned like reference numerals.

DETAILED DESCRIPTION OF THE PREFERRED EMBODIMENTS

Figure 2:
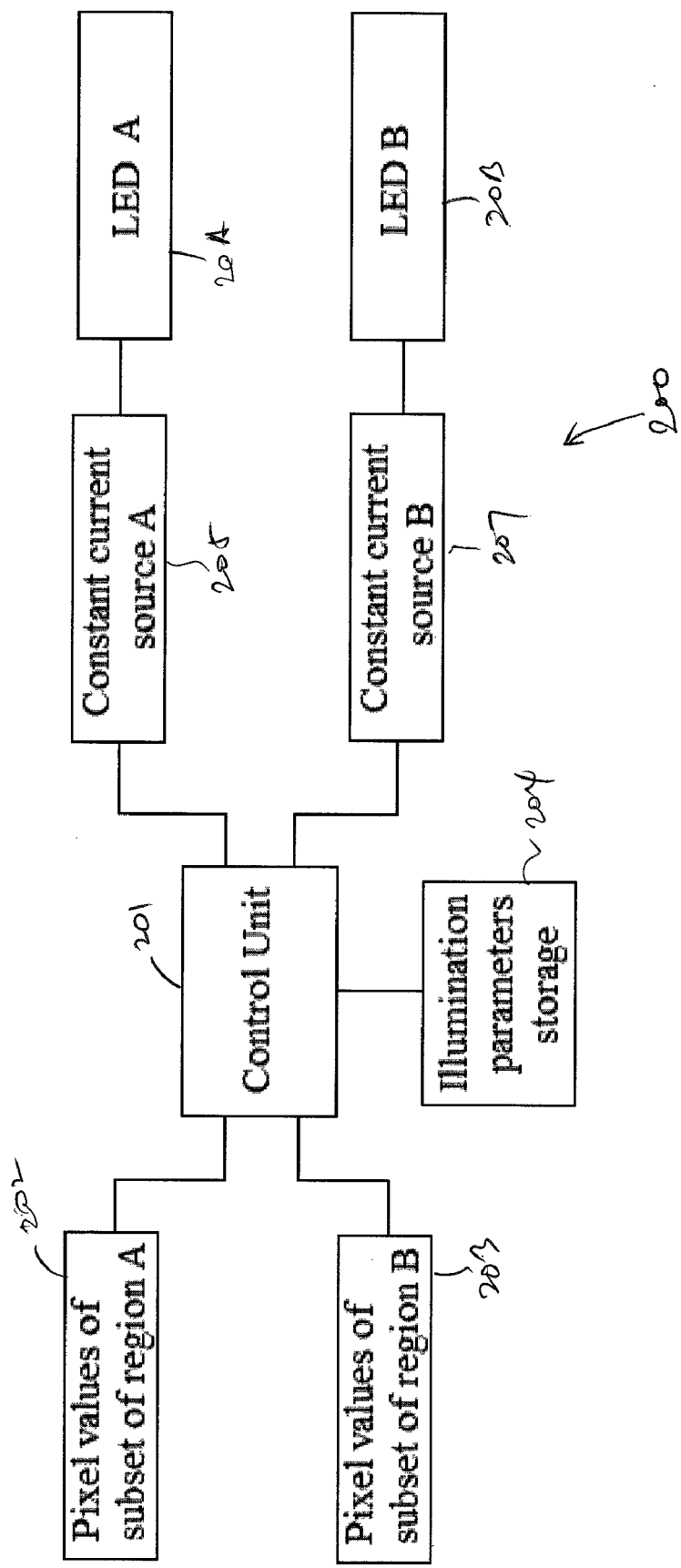
FIG. 2 illustrates exemplary control scheme 200 for driving the LED's of capsule camera 100 (e.g., LEDs 20A and 20B of FIGS. 1A and 1B), in accordance with one embodiment of the present invention.

FIG. 1A shows capsule camera 100 inside a gastrointestinal tract 10 taking measurements with its light emitting diode (LED) light sources 20A and 20B. As shown in FIG. 1A, capsule camera 100 includes housing 107, LEDs 20A and 20B, baffler/reflector 108, and image sensor 21. Image sensor 21 may include more than one sensor array. The image on image sensor 21 is processed by image processor 102 using digital signal processing techniques. Selected images are compressed in image compression module 103 and stored into memory 104. Power supply 105 provides power for capsule camera 100's operations. After capsule camera 100 is recovered, output port 106 allows a user to upload to a workstation the stored images and other data. In another embodiment, instead of storing the images on-board, a transmitter is provided in capsule camera 100 which transmits the image data to a receiver outside of the patient's body, where the images may be processed or archived for later review. The present invention is applicable to both systems that store the image data on-board and systems that transmit the image data.

The amount of light provided for each exposure is given by the sum of the light provided by all the LEDs. The light provided by each LED is the product of the LED "on" time and its intensity. By adjusting the amounts of light provided in LEDs 20A and 20B, it is desired that image of point B (which is far away), resulting from the light reflected from point B onto image sensor 21, is not under-exposed, and the image of point A (which is much closer), from light reflected from point A, is not over-exposed. GI tract 10 is not a uniform pipe, but includes both wide and narrow portions. FIG. 1B shows, for example, capsule camera 100 in narrow portion 11 of GI tract 10. In portion 11, LED light sources 20A and 20B are kept at suitable lighting levels, so that the image of illuminated objects at image sensor 21 is not over-exposed, and to save battery power.

It is significant that, for each capsule endoscopic procedure, tens to hundreds of thousands of images are taken and stored, thus requiring a large amount of physician time to read and archive the images. During the procedure, which normally takes from a few hours to more than 10 hours, a capsule camera continues to take pictures of the GI tract at the rate of one to a few frames per second, as it travels by peristalsis activities of the GI tract. The total number of images taken ranges from tens of thousands to hundreds of thousands. Even if software is provided in the workstation to accelerate the physician's or technician's viewing process, tens of minutes of physician or technician time is still required to examine these images. The requirements for archiving, retrieval and transferring large amount of data is also severe. Moreover, for each image, power is also required for lighting, image processing and storing. As capsule camera 100 does not move or moves very little relative to GI tract 10 much of the time, camera 100 records an image only when a significant movement is detected relative to the last image.

Capsule camera 100, however, is still required to take images for use in motion detection. There is a range of exposures that result in clear pictures suitable for review by human eyes. At a lower exposure (i.e., under an under-exposure condition), the human eyes are not efficient. However, so long as the lower exposure is above the system noise level, image processing techniques may be applied to the image data to differentiate features in the image, even if the image is too dark for human eyes. Such an image may still be used to detect motion. Therefore, lighting may be reduced for motion detection images, which are not used for a physician's later analysis. Further, for such purpose, only some of the LED's of the lighting system need to be on, and only images of a portion of the entire field of view need be acquired for the capsule camera's motion detection circuits. The capsule camera returns to normal lighting conditions when it determines that significant movement has occurred.

Images taken for the purpose of motion detection need only involve a subset of the pixels on image sensor 21, and the exposure provided for each pixel may be much lower than that required for an image intended for physician review. Thus, for motion detection images, the power output of LED light sources 20A and 20B may be a fraction of that required for an image suitable for human review. Moreover, the subset of pixels on image sensor 21 used for motion detection may be selected from specified areas of the pixel array or arrays, where one of the lighting sources 20A and 20B—the one having a higher percentage of light reaching the region in the field of view corresponding to the subset of pixels—needs to be activated. Because only a smaller number of pixels of the whole image are involved in acquisition and processing motion detection images, power is reduced. The motion detection images are discarded, so that a physician's time spent in reviewing and archiving redundant images is reduced.

Autonomous capsule camera 100 operates from a power source. Normally, the power source may be a battery system, or a changing magnetic field imposed from outside which is used by the power supply circuits in the capsule to generate power. Because it is desirable that the procedure is performed as an out-patient procedure with the patient ambulatory, the battery approach is preferred. Normally, the size of capsule camera 100 is limited by the physical size of the battery. A higher detection rate requires a higher resolution and a higher frame rate, which in turn demand a larger battery capacity with larger dimensions. Power saving achieved when the capsule is quiescent (i.e., not moving) enables using a smaller capsule camera, thus making it easier to swallow. Such a capsule camera is desirable for use especially by a child, an elderly person, or a very sick patient. Such a smaller capsule camera also enhances the detection rate. Thus power conservation is practiced whenever possible without compromising performance.

In FIG. 1A, the lighting near point A is primarily provided by LED 20A, while around points B and C, the light is primarily provided by LED 20B. To avoid an over-exposure at the image of point A, LED 20A should be adjusted to a lower light level to avoid an overly bright and saturated image. Conversely, around points B and C, LED 20B must provide a stronger lighting. Relative to point A, a proper exposure of points B and C require a higher intensity or a longer exposure time, or both. By the same principles, in FIG. 1B, where the space is much smaller, the light intensities of both 20A and 20B should be adjusted to be much lower.

Inside the GI tract, capsule camera 100 may move forward (and at times backward), rotate or move in other ways. The movements are generally slow, however. Therefore, if the images are taken at a fast enough rate, capsule camera 100's position relative to the GI tract change little from one image to the next. Lighting may therefore be adjusted for all regions of interest by controlling the driving parameters to all LED's accordingly in a continuous fashion.

FIG. 2 illustrates exemplary control scheme 200 for driving the LED's of capsule camera 100 (e.g., LEDs 20A and 20B of FIGS. 1A and 1B), in accordance with one embodiment of the present invention. After the exposure of a previous frame, control unit 201 (e.g., image processor 102) analyzes a selected region covered by LED 20A, using pixel values at pixel subset 202 of the image for that region. If the image is over- or under-exposed, an adjustment to achieve the appropriate lighting is determined for the next image. (The pixel value is expected to be in linear proportion to the exposure). The same procedure is performed for another selected region, which is covered by LED 20B using pixel values at pixel subset 203 of the image. The parameters for a proper exposure are then stored in medium 204 (e.g., flip-flops, registers or another temporary storage medium). In one implementation, one exposure parameter is the "on" duration for an LED (e.g., LEDs 20A or 20B) that is driven by a constant current source (current source 205 or 206). Such an arrange results in a simple driving circuit design. Other schemes—such as, for example, increasing the light intensity of an LED by providing a higher current—are also possible.

Figure 3:
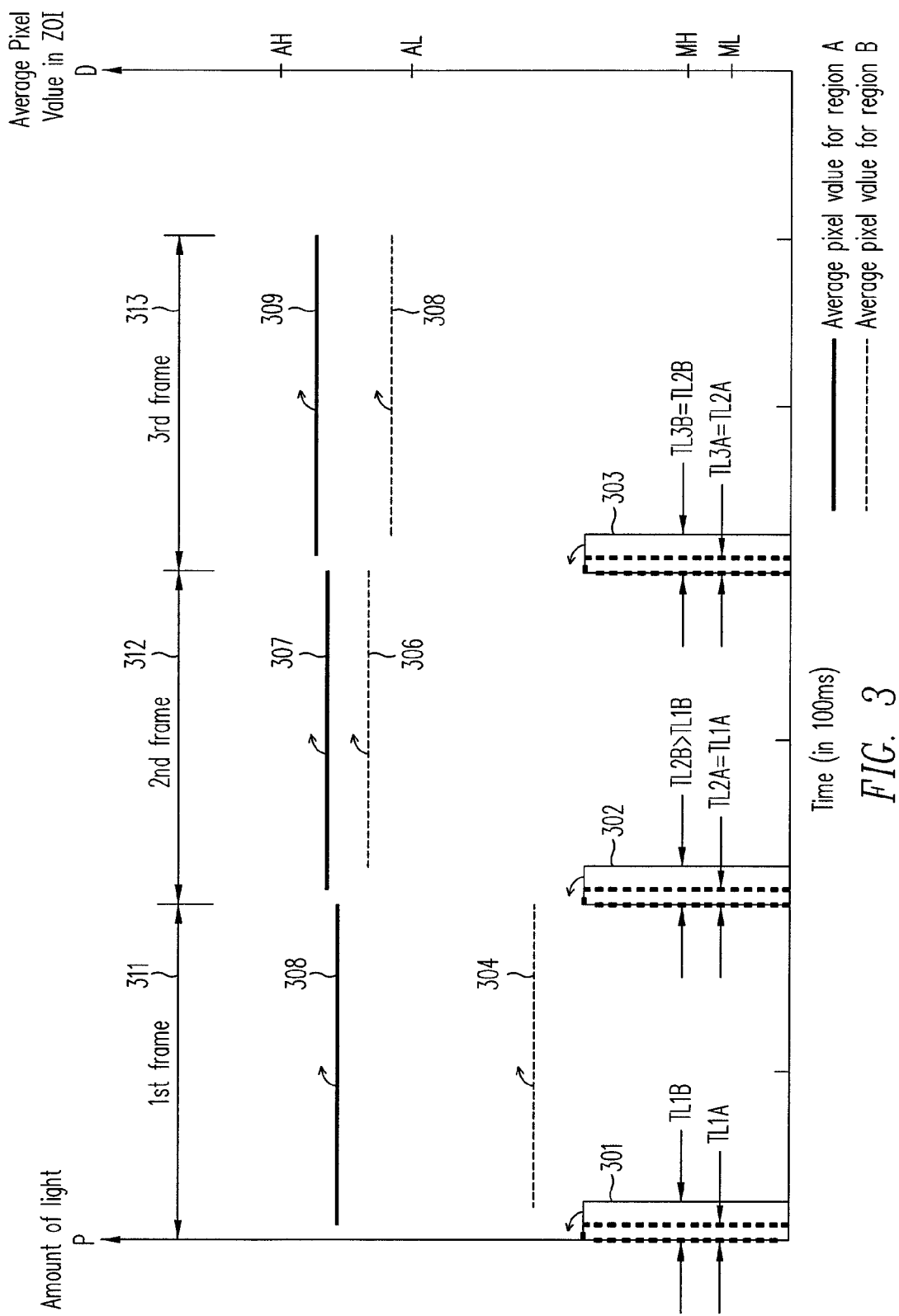
FIG. 3 shows amounts of light 301, 302 and 303 provided to the LEDs of capsule 100 for taking consecutive frames 311, 312 and 313 under the control scheme of FIG. 2.

FIG. 3 illustrates consecutive frames 311, 312 and 313 taken under the control scheme of FIG. 2. FIG. 3 shows both quantities expressed in pixel values (referring to the axis on the right) and quantities expressed in light intensity (referring to the axis on the left). The pixel value for this purpose may be selected from those that can be taken from the image with a reasonable amount of image processing. One example is the average value of a subset of pixels in a region covered by a light source. Alternatively, the pixel value may correspond to the highest occurrence, or another parameter that represents the total brightness. In this detailed description, the average pixel value is used merely for illustrative purposes. Other parameters may be used within the scope of the present invention. On the right axis, AH and AL indicate, respectively, the upper bound and the lower bound of the range of pixel values suitable for human review and analysis. ML represents the brightness below which the noise in the system interferes with the capsule camera's ability to handle the image processing necessary for the light control. MH is an upper bound set for the motion detection exposures, selected to most effectively save power.

FIG. 3 shows amounts of light (i.e., exposures) 301, 302 and 303 provided by the LEDs of capsule camera 100 for frames 311, 312 and 313, respectively. In FIG. 3, the luminances or intensities of LEDs 20A and 20B are kept constant, so that exposures 301, 302 and 303 can be controlled by the durations at LED 20A (TL1A, TL2A and TL3A) and the durations at LED 20B (TL1B, TL2B and TL3B), when LEDs 20A and 20B are turned on, respectively. After frame 311 is taken, control unit 201 obtains the average pixel values 304 and 305 from the image at the pixel subsets covered by LEDs 20A and 20B, respectively. As shown in FIG. 3, average pixel value 304 for the region covered by LED B is below AL. Thus, control unit 201 calculates the proper amount of light (i.e. exposure time in this case, as the LEDs have constant luminance) for the next frame, assuming the same scene. For the same scene, the average pixel value depends linearly on the amount of light. As average pixel value 305 for region A is within the range between AH and AL, no adjustment to the exposure time is required for LED 20A. As average pixel values 306 and 307 for frame 312 are within the range between AH and AL, no adjustment to exposure times for LEDs 20A and 20B are provided to take frame 313.

Figure 4:
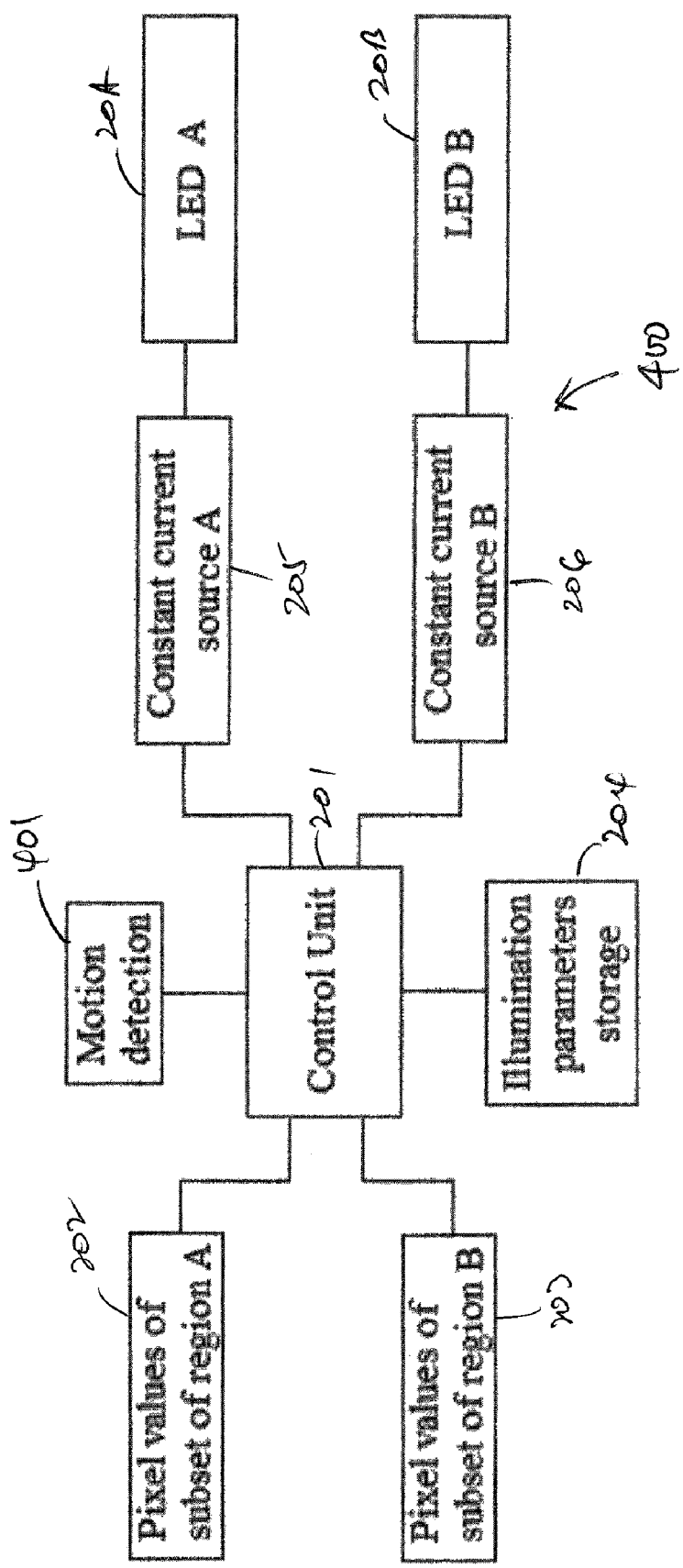
FIG. 4 shows control scheme 400 which includes motion detection function 401, in accordance with one embodiment of the present invention.

FIG. 4 shows control scheme 400 which includes motion detection function 401, in accordance with one embodiment of the present invention. Motion detection function 401 achieves power savings in the operations of capsule camera 100 by storing or transmitting an image only when the image shows a significant movement relative to a previous image. Motion detection function 401 may be implemented in a variety of ways. Some methods for motion detection are disclosed, for example, in co-pending U.S. patent application, entitled "IN VIVO AUTONOMOUS CAMERA WITH ON-BOARD DATA STORAGE OR DIGITAL WIRELESS TRANSMISSION IN REGULATORY APPROVED BAND," Ser. No. 11/533,304, filed on Sep. 19, 2006. The copending application is hereby incorporated by reference in its entirety. Motion detection detects whether or not a significant enough movement has occurred within the field of view of interest. When there is no movement, the next frame would be taken in the monitor mode, in which the amount of light for the exposures is reduced to a level such that the pixel values in the image for regions A and B are between MH and ML. This amount of light is selected to be low but sufficient to allow control unit 201 to reliably determine if a significant movement has taken place. In the monitor mode, if any movement is detected, control unit 201 returns to an active mode to capture an image that is within the range for human review. In some embodiments, in the monitor mode, not all the LED's are turned on, as is the case in the active mode. In practice, a single LED provides sufficient light to detect motion.

Figure 5:
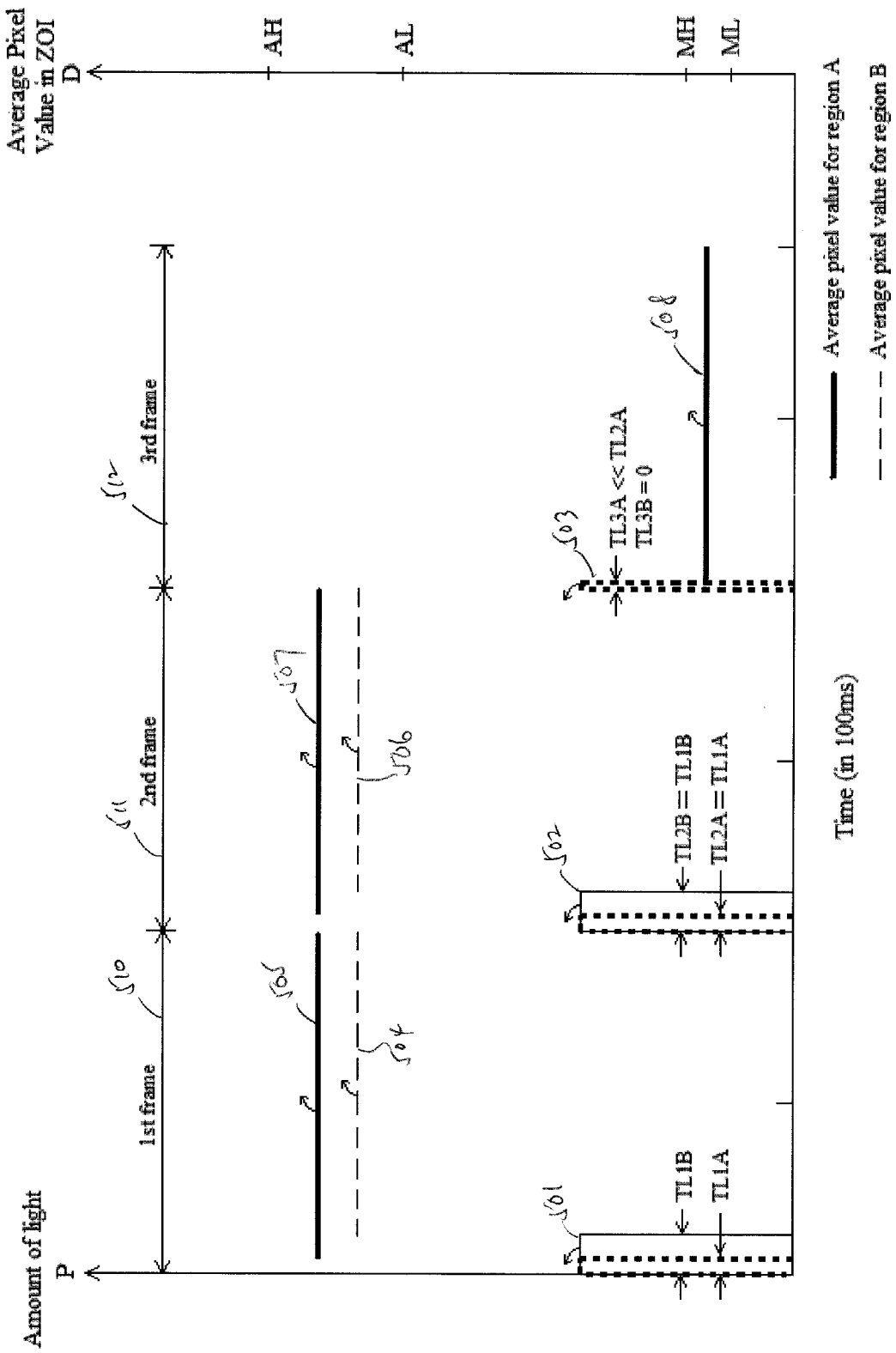
FIG. 5 illustrates amounts of light 501, 502 and 503 provided by the LEDs of capsule camera 100 for taking frames 510, 511 and 512, under the control scheme of FIG. 4.

It is possible that, at the first frame taken after entering into the monitor mode, capsule camera 100 actually moves. The pixel value in a region covered by one turned-on LED is linearly dependent on the amount of light provided by the LED. Therefore, in some embodiments, the average pixel values in the same region covered by the turned-on LED may still be compared to detect motion between the last frame taken before entering the monitor mode and the first frame after entering the monitor mode. This is achieved by scaling the average pixel value in the last frame of the active mode according to the amounts of light provided by the LED in the two frames. FIG. 5 shows amounts of light 501, 502 and 503 provided by the LEDs of capsule camera 100 for taking frames 510, 511 and 512, under control scheme 400 of FIG. 4. As shown in FIG. 5, the same amounts of light 501 and 502 are provided by LEDs 20A and 20B for taking frames 510 and 511. Control unit 201 detects that no motion occurred between frames 510 and 511, and thus enters into monitor mode after frame 511. An amount of light 503, which is provided only by LED 20A, is used for illuminating the field of view in the monitor mode. LED 20B is turned off to save power. To detect if motion occurred between frames 511 and 512, the average pixel value 507 for region A of frame 511 is scaled by the ratio TL3A:TL2A, which is the ratio of exposure times for taking frames 511 and 512. The scaled average pixel value is then compared to measured average pixel value 508 of frame 512. If motion is detected, control unit 201 returns to active mode after just one frame in monitor mode. Because a slight error may exist in the driving circuit (i.e., the actual deliveries of the two different light amounts may not be exactly according to the predetermined ratio), in some embodiments, the threshold selected for motion detection between two frames in different modes may be different from the threshold selected for motion detection in the active mode, when the amount of light does not change between two frames. Similarly, different thresholds of motion detection may be used between two frames of the same light amount and between two frames of different light amounts, even in the same mode.

In one embodiment, the motion detection function uses the average pixel value of the last frame before entering the monitor mode to compare with the average pixel value of a current frame. In this method, one or more frames may have been taken in the monitor mode that the motion detection function cannot detect a significant movement from frame to frame. However, when the average pixel value of the current frame is compared to the last frame before entering the monitor mode, the accumulated difference in the average pixel value may be sufficient to reach the threshold of motion detection. At that point, capsule camera 100 returns to active mode to capture an image that a physician can review.

Figure 6:
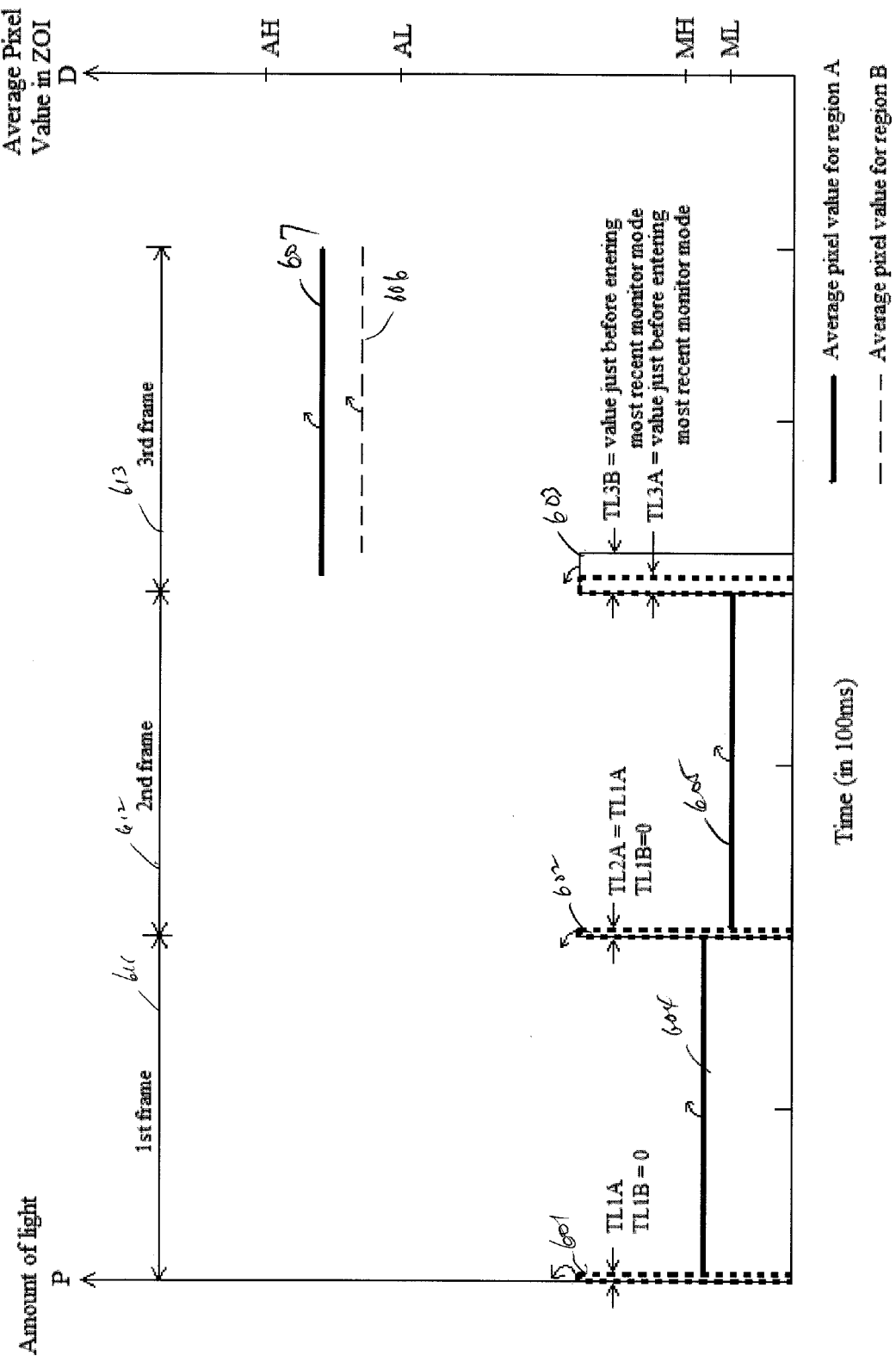
FIG. 6 shows lights amounts 601, 602 and 603 provided by the LEDs of capsule camera 100 under control scheme 400 of FIG. 4; light amounts 601 and 602 being provided in the monitor mode and light amount 603 being provided after returning to the active mode.

FIG. 6 shows lights amounts 601, 602 and 603 provided by the LEDs of capsule camera 100 under control scheme 400 of FIG. 4; light amounts 601 and 602 being provided in the monitor mode and light amount 603 being provided after returning to the active mode. In FIG. 6, motion is detected between frames 611 and 612. Therefore, control unit 201 returns to the active mode and takes frames using both LEDs 20A and 20B using, for each LED, the same light amount used for taking the last frame prior to entering the monitor mode. In the active mode, control unit 201 stays in the active mode as long as movement is detected between two consecutive frames. It is possible that the first frame taken in the active mode shows no movement from the last frame taken in the monitor mode. In that situation, control unit 201 returns to the monitor mode after only one frame in the active mode. Alternatively, for the first frame in the active mode following the monitor mode, the light amount provided by LED 20A is determined from scaling the light amount used for the last frame in the monitor mode, and the light provided by LED 20B is the light amount provided by LED 20B for the last frame the previous time control unit 201 was in the active mode.

In one embodiment, the image is low-pass filtered before performing motion detection in the monitor mode, so as to reduce the noise. A lower noise level allows a further reduction of the MH and ML levels. In another implementation, adjacent pixels are resampled to subdue noise to lower the MH and ML levels. For example, a 64×64 sub-region may be resampled by combining (e.g., summing) 4 adjacent pixels to achieve a 32×32 sub region, which may then be used for motion detection.

Figure 7A:
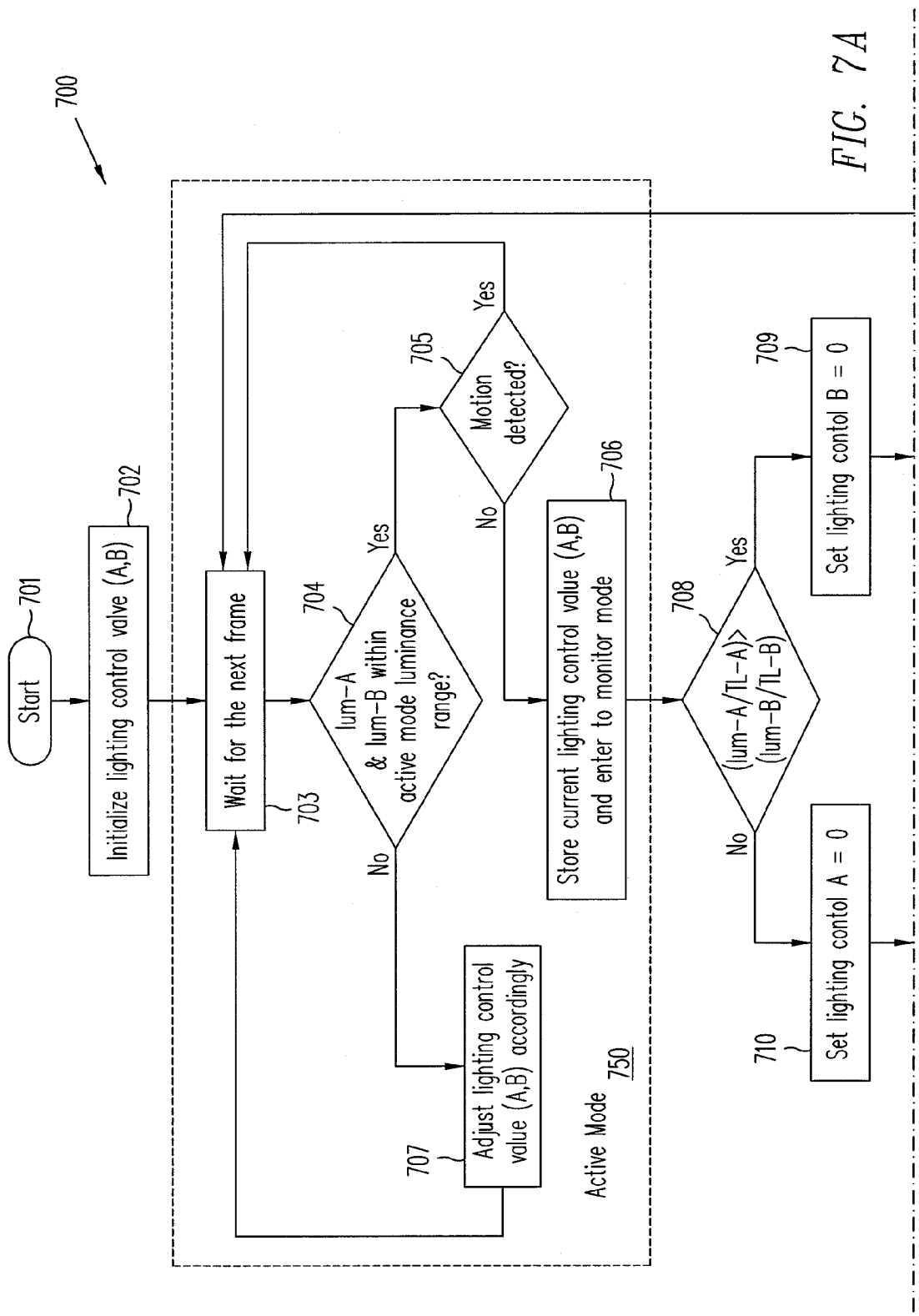
FIG. 7 is a flow chart illustrating the operations of control unit 201 both in the monitor mode and the active mode, in accordance with one embodiment of the present invention.
Figures 7, 7B:
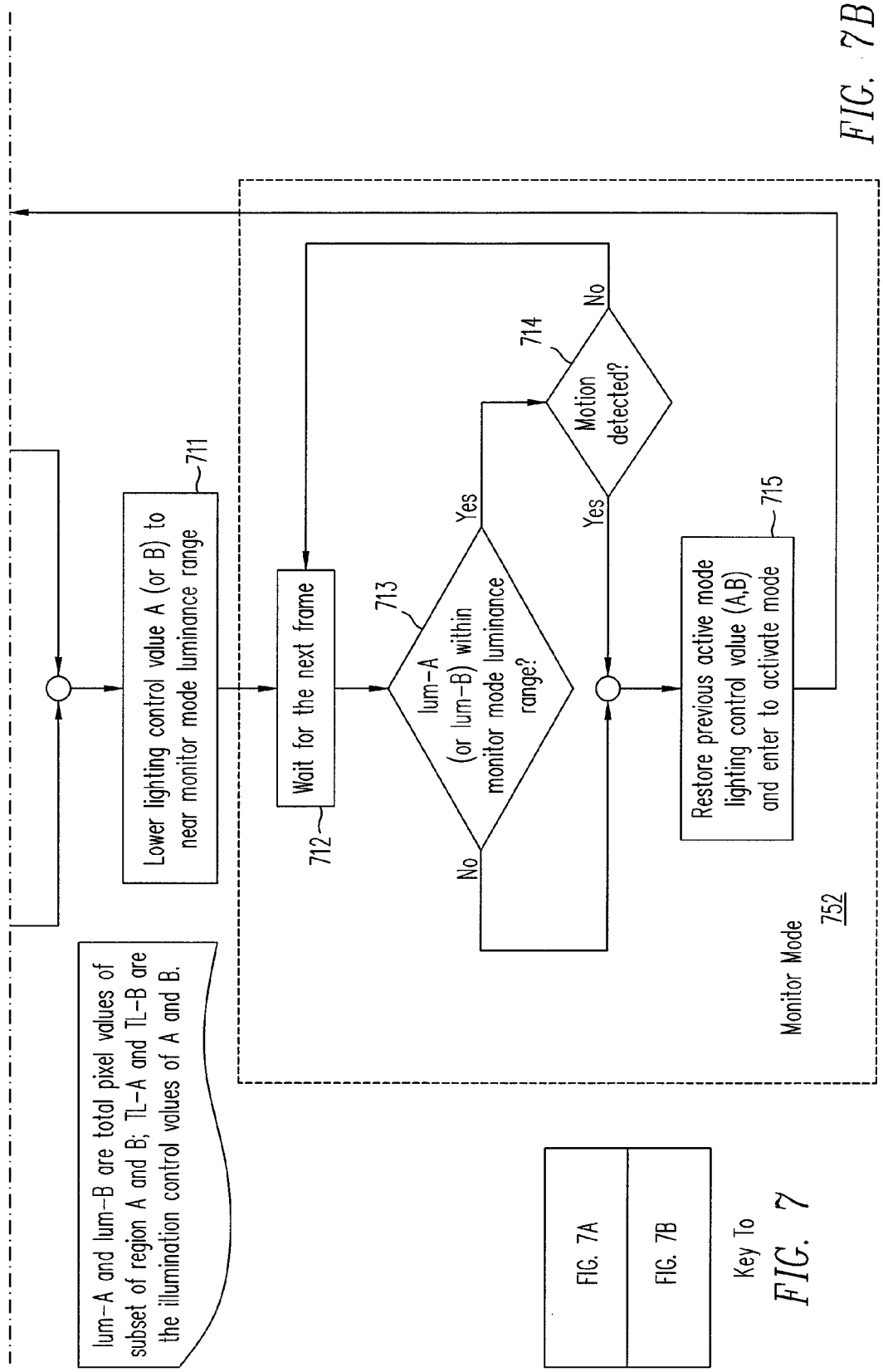

FIG. 7 is a flow chart illustrating the operations of control unit 201 in both the monitor mode and the active mode, in accordance with one embodiment of the present invention. In the embodiment of FIG. 7, LEDs 20A and 20B and two regions illuminated respectively by these LEDs are used to control the operations. For illustrative purpose only, LEDs 20A and 20B are modeled as constant current sources, so that each LED's turned-on duration (i.e., exposure time) determines the amount of light provided by the LED in each frame. In another embodiment, in which the current may be varied, the amount of light provided is the variable light intensity integrated over the exposure period. Of course in all the embodiments, the exposure time precedes the image data acquisition, processing, transmission and storage function. As shown in FIG. 7, operations 703-707 are carried out in active mode 750 and operations 712-716 are carried out in monitor mode 752.

In active mode 750, when a frame is taken at step 703, the response or pixel values lum-A and lum-B derived from regions A and B, respectively, are examined at step 704 to determine if they are each within the active mode luminance range (e.g., between AH and AL of FIG. 6). If the pixel values are within the active mode luminance range, the motion detection function examines if motion has occurred between the present frame and a previous frame (step 705). If one or more of the pixel values are not within the active mode luminance range, the appropriate lighting control value or values (e.g., the LED "on" time or times) are adjusted, where necessary, to bring the pixel values back to within range (step 707). If motion is not detected (step 706), the lighting control values for LEDs 20A and 20B are stored, and control unit 201 exits active mode 750. Otherwise, control unit 201 returns to step 703 to wait for the next frame to be taken.

In one embodiment, when motion is detected, the mage is stored or transmitted even when the pixel values are not within the desired range (e.g., between AH and AL as shown in FIG. 6). In another embodiment, when motion is detected, only image regions where average pixel values are in the desired range (i.e., between AH and AL) are stored or transmitted. Image regions where the pixel values are out of the desired range are discarded. In still another embodiment, the range used at step 704 to determine if the lighting should be adjusted may be different from the range used to determine if an image is to be stored or transmitted.

Upon leaving active mode 750, the pixel values for regions A and B and the light amounts provided are examined (step 708) to determine which of regions A and B has a larger pixel value to light amount ratio. The LED which results in the lesser response is turned off (step 709 or step 710) before entering into monitor mode 752. At step 711, the appropriate lighting control value in monitor mode 752 for the other LED (i.e., the LED which provide the greater pixel value to light amount ratio from regions A and B) is set.

In monitor mode 752, when a frame is taken in step 712, the response or pixel value lum-A or lum-B derived from the active one of regions A and B is examined at step 713 to determine if it is within the monitor mode luminance range (e.g., between MH and ML of FIG. 6). If the pixel value is within the active mode luminance range, the motion detection function examines if motion has occurred between the present frame and a previous frame (step 714). If motion is detected (step 715), the stored lighting control values for LED 20A and 20B from active mode 750 are restored, and control unit 201 exits monitor mode 752. Otherwise, control unit 201 returns to step 712 to wait for the next frame to be taken.

Figure 8:
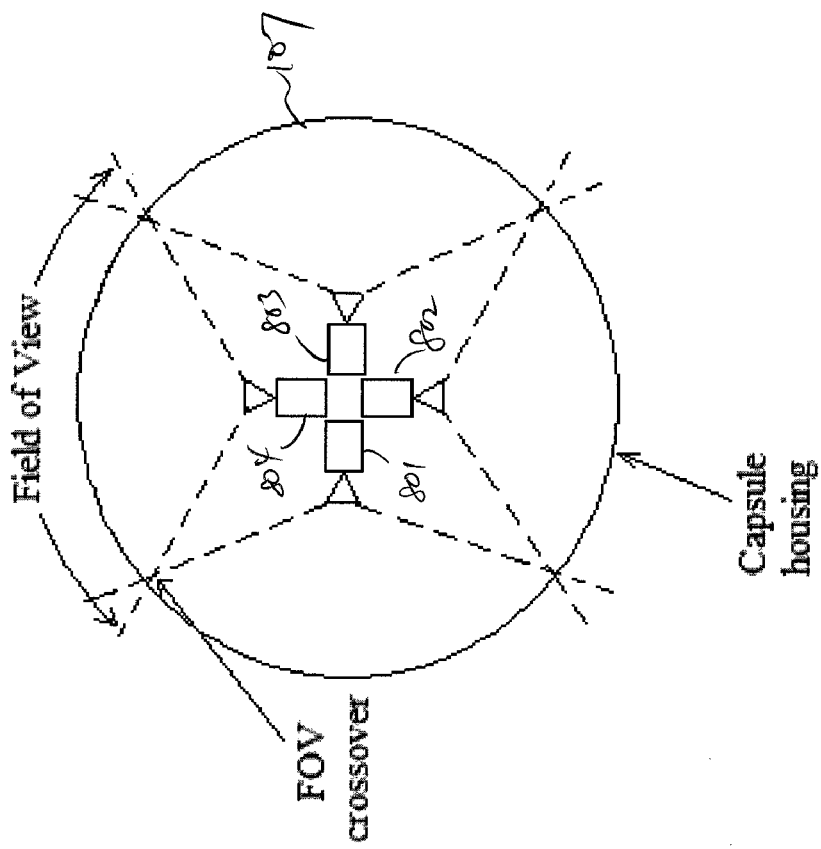
FIG. 8 is a cross section of housing 107 of capsule camera 100, showing cameras 801-804 each facing outward in a different direction, thereby compositing a panoramic view.

More than two LEDs are expected to be used in a practical implementation of capsule camera 100. There may also be more than one image sensor array. FIG. 8 is a cross section of housing 107 of capsule camera 100, showing cameras 801-804 each facing outward in a different direction, thereby compositing a panoramic view. As cameras 801-804 each have a field of field that is more than 90 degrees wide, and so long as the fields of views of adjacent cameras overlap inside capsule housing 107, a 360-degree total field is provided perpendicular to the longitudinal direction in which capsule camera 100 travels. The current state-of-the-art is capable of providing lens and sensor arrays that are each in the order of 1 mm in each dimension. Using these components, capsule camera 100 may be implemented with housing 107, which may have a 1-cm diameter.

Figure 9:
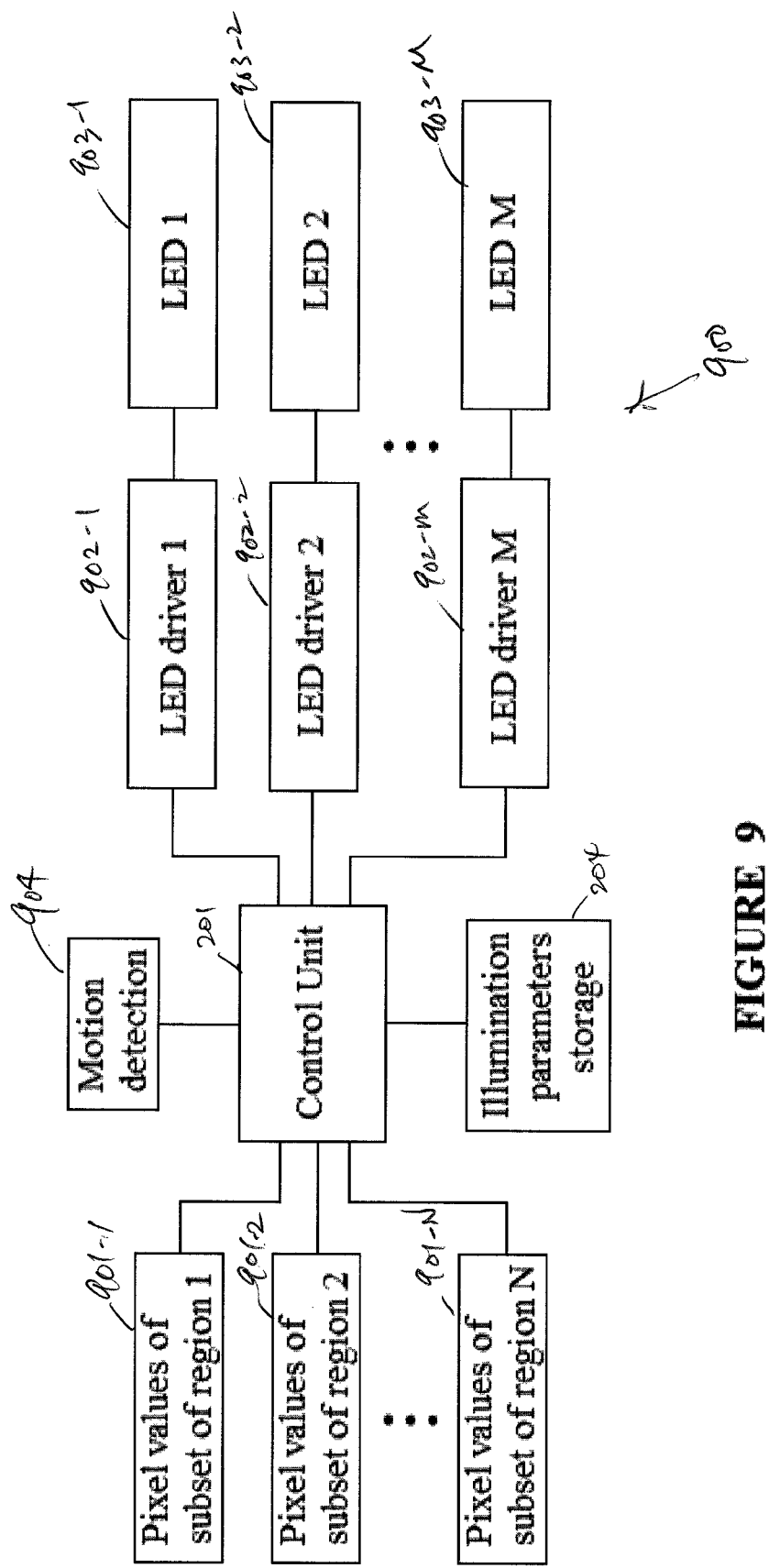
FIG. 9 shows lighting control scheme 900, having N separate regions 901-1 to 901-N illuminated by LEDs 903-1 to 903-M, according to one embodiment of the present invention.

FIG. 9 shows lighting control scheme 900, having N separate regions 901-1 to 901-N illuminated by LEDs 903-1 to 903-M, according to one embodiment of the present invention. The images of regions 901-1 to 901-N may situate in different sensor arrays, with each region receiving light from one or more LED's. When entering into the monitor mode, some of the LED's may be turned off to save power. The motion detection circuits 904 may compare, using successive images, subsets of pixel values in one or more regions.

Figure 10A:
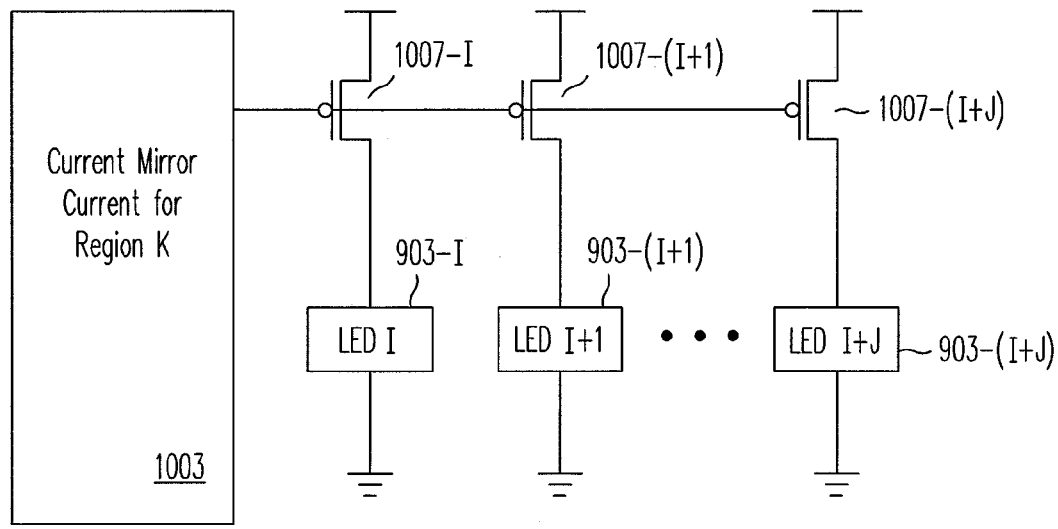
FIGS. 10A and 10B show respectively designs 1001 and 1005 each providing different constant driving currents for LEDs 903-I, 903-(I+1), ..., 903-(I+J) to illuminate specified region K, in accordance with one embodiment of the present invention.
Figure 10B:
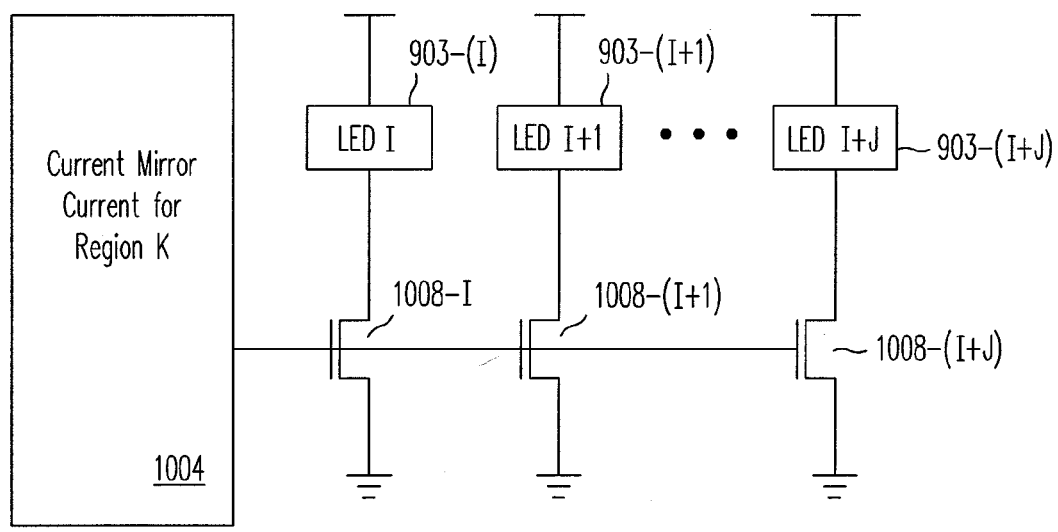

The power requirement for an LED constant current driver includes a constant current source in a current mirror circuit. Resistors in the constant current source are normally selected to have very high values so as to reduce the operating current of the constant current source. Since a conventional semiconductor process does not reliably provide high-value resistors with good precision, such resistors are typically implemented outside the integrated circuit by discrete components. In a capsule camera, where space is limited, these resistors and their interconnections with the integrated circuit may cause space and manufacturing difficulties. FIGS. 10A and 10B show respectively designs 1001 and 1005 each providing different constant driving currents for LEDs 903-I, 903-(I+1), . . . , 903-(I+J) to illuminate specified region K, in accordance with one embodiment of the present invention. In each of designs 1001 and 1005, the current in the current mirror circuit (i.e., current mirror circuit 1003 or current mirror circuit 1004) is reflected in (J+1) currents to drive LEDs 903-I, 903-(I+1), ..., 903-(I+J). Design 1001 provides the currents through PMOS transistors 1007-I, 1007-(I+1), ..., 1007-(I+J). Similarly, design 1002 provides the currents through NMOS transistors 1008-I, 1008-(I+1), ..., 1008-(I+J). In these designs, one current mirror circuit is provided for each given region to drive multiple LEDs, so as to save space and improve manufacturing yield.

The above detailed description is provided to illustrate the specific embodiments of the present invention and is not intended to be limiting. Numerous variations and modifications within the scope of the present invention are possible. The present invention is set forth in the following claims:

I claim:

1. A capsule camera having adjustable illumination control, comprising:
    one or more sensor arrays each having one or more pixels in one or more designated regions in a field of view of the capsule camera;
    a plurality of lighting elements each providing illumination to one or more of the designated regions wherein the illumination intensity and duration for a given image frame are determined from an evaluation of a previous image frame; and
    a control unit that (a) extracts from the given image one or more parameter values that represent detected energy from the pixels of each region in the image; (b) evaluates the parameter values at each region; and (c) adjusts each lighting element according to the evaluation to provide illumination to each region in taking a subsequent frame of image.

2. A capsule camera as in claim 1, wherein the parameter value is an average value of the pixels.

3. A capsule camera as in claim 1, wherein the adjustment attempts to bring the parameter value for the region to within a predetermined range.

4. A capsule camera as in claim 1, wherein the control unit adjusts an amount of light provided by each lighting element.

5. A capsule camera as in claim 4, wherein the amount of light is provided by integrating a light intensity of the lighting element over time.

6. A capsule camera as in claim 5, wherein the light intensity is substantially constant and wherein the control unit adjusts an exposure time for each lighting element.

7. A capsule camera as in claim 1, wherein the lighting element comprises a light emitting diode.

8. A capsule camera as in claim 1, further comprising a motion detection circuit which compares the extracted parameter values in two exposures to detect motion of the capsule camera.

9. A capsule camera as in claim 8, wherein the exposures are two successive exposures of the capsule camera.

10. A capsule camera as in claim 8, wherein the control unit operates in an active mode and a monitor mode, the control unit entering the monitor mode when no motion of the capsule camera is detected in successive exposures in the active mode, and entering the active mode when motion is detected in the monitor mode.

11. A capsule camera as in claim 10, wherein images used for detecting motion in the monitor mode are at a lower resolution.

12. A capsule camera as in claim 11, wherein the lower resolution is achieved by combining adjacent pixels.

13. A capsule camera as in claim 10, wherein exposures in the active mode are provided within a first range of light amounts and exposures in the monitor mode are provided in a second range of light amounts, the light amounts within the first range being substantially greater than the light amounts in the second range.

14. A capsule camera as in claim 13, wherein the first range is provided to yield images with luminance for a human reviewer to perform a diagnosis.

15. A capsule camera as in claim 13 wherein, in the first exposure of the monitor mode, the parameter value extracted from the last exposure in the active mode is scaled based on the first and second ranges of light amounts for use by the motion detection circuit in the comparison.

16. A capsule camera as in claim 15 wherein, in the monitor mode, the motion detection circuit compares the extracted parameter value for each frame against the parameter value extracted from the last exposure in the active mode.

17. A capsule camera as in claim 10, wherein the criteria for motion detection in the active mode and in the monitor mode are different.

18. A capsule camera as in claim 10, wherein the criterion for motion detection for successive frames with the same exposure is different from the criterion for motion detection for successive frames with different amounts of exposure.

19. A capsule camera as in claim 10 wherein, upon returning to the active mode from the monitor mode, the lighting elements are returned to settings used for taking the last frame in a previous active mode operation.

20. A capsule as in claim 19, wherein the setting are stored for later retrieval in the capsule camera upon leaving the previous active mode.

21. A capsule camera as in claim 10, wherein one or more of the lighting elements are not activated in the monitor mode.

22. A capsule camera as in claim 1, wherein the capsule camera comprises a plurality of component cameras each facing a different direction.

23. A capsule camera as in claim 22, wherein the fields of view of the component cameras together provide a panoramic field of view.

24. A capsule camera as in claim 23, wherein the panoramic field of view is 360-degree.

25. A capsule camera as in claim 1, wherein each designated region is illuminated by a plurality of lighting elements.

26. A capsule camera as in claim 25, wherein each lighting element illuminates a designated region driven by a common current mirror circuit.

27. A capsule camera as in claim 26, wherein the current in each lighting element is reflected from the common current mirror circuit by a transistor of a predetermined conductivity type.

28. A method in a capsule camera for providing adjustable illumination control, comprising:
    providing one or more sensor arrays each having one or more pixels in one or more designated regions in a field of view of the capsule camera;
    providing a plurality of lighting elements each providing illumination wherein the illumination intensity and duration for a given image frame are determined from an evaluation of a previous image frame to one or more of the designated regions;
    extracting from an image one or more parameter values that represent detected energy from the pixels of each region in the image;
    evaluating the parameter values at each region; and
    adjusting each lighting element according to the evaluation to provide illumination to each region in taking a subsequent frame of image.

29. A method as in claim 28, wherein the parameter value is an average value of the pixels.

30. A method as in claim 28, wherein the adjusting attempts to bring the parameter value for the region to within a predetermined range.

31. A method as in claim 28, wherein the adjusting adjusts an amount of light provided by each lighting element.

32. A method as in claim 31, wherein the amount of light is provided by integrating a light intensity of the lighting element over time.

33. A method as in claim 32, wherein the light intensity is substantially constant and wherein the adjusting adjusts an exposure time for each lighting element.

34. A method as in claim 28, wherein the lighting element comprises a light emitting diode.

35. A method as in claim 28, further comprising detecting motion by comparing the extracted parameter values in two exposures to detect motion of the capsule camera.

36. A method as in claim 35, wherein the exposures are two successive exposures of the capsule camera.

37. A method as in claim 35, wherein the capsule camera operates in an active mode and a monitor mode, the capsule camera entering the monitor mode when no motion of the capsule camera is detected in successive exposures in the active mode, and entering the active mode when motion is detected in the monitor mode.

38. A method as in claim 37, wherein images used for detecting motion in the monitor mode are at a lower resolution.

39. A method as in claim 38, wherein the lower resolution is achieved by combining adjacent pixels.

40. A method as in claim 37, wherein exposures in the active mode are provided within a first range of light amounts and exposures in the monitor mode are provided in a second range of light amounts, the light amounts within the first range being substantially greater than the light amounts in the second range.

41. A method as in claim 40, wherein the first range is provided to yield images with sufficient luminance for a human reviewer to perform a diagnosis.

42. A method as in claim 40 wherein, in the first exposure of the monitor mode, the parameter value extracted from the last exposure in the active mode is scaled based on the first and second ranges of light amounts for use in the comparison.

43. A method as in claim 42 wherein, in the monitor mode, the comparing compares the extracted parameter value for each frame against the parameter value extracted from the last exposure in the active mode.

44. A method as in claim 37, wherein the criteria for motion detection in the active mode and in the monitor mode are different.

45. A method as in claim 37, wherein the criterion for motion detection for successive frames with the same exposure is different from the criterion for motion detection for successive frames with different amounts of exposure.

46. A method as in claim 37 wherein, upon returning to the active mode from the monitor mode, the lighting elements are returned to settings used for taking the last frame in a previous active mode operation.

47. A method as in claim 46, wherein the setting are stored for later retrieval in the capsule camera upon leaving the previous active mode.

48. A method as in claim 37, wherein one or more of the lighting elements are not activated in the monitor mode.

49. A method as in claim 28, further comprising providing in the capsule camera a plurality of component cameras each facing a different direction.

50. A method as in claim 49, wherein the fields of view of the component cameras together provide a panoramic field of view.

51. A method as in claim 50, wherein the panoramic field of view is 360-degree.

52. A method in claim 28, wherein each designated region is illuminated by a plurality of lighting elements.

53. A method as in claim 52, wherein each lighting element illuminates a designated region driven by a common current mirror circuit.

54. A method as in claim 53, wherein the current in each lighting element is reflected from the common current mirror circuit by a transistor of a predetermined conductivity type.

\* \* \* \* \*